(12) United States Patent
Zhang et al.

(10) Patent No.: US 10,803,584 B2
(45) Date of Patent: Oct. 13, 2020

(54) METHOD AND APPARATUS FOR ACQUIRING INFORMATION

(71) Applicant: Baidu Online Network Technology (Beijing) Co., Ltd., Beijing (CN)

(72) Inventors: Shaoting Zhang, Beijing (CN); Weidong Zhang, Beijing (CN); Qi Duan, Beijing (CN)

(73) Assignee: Baidu Online Network Technology (Beijing) Co., Ltd., Beijing (CN)

( * ) Notice: Subject to any disclaimer, the term of this patent is extended or adjusted under 35 U.S.C. 154(b) by 133 days.

(21) Appl. No.: 16/130,316

(22) Filed: Sep. 13, 2018

(65) Prior Publication Data

US 2019/0114771 A1 Apr. 18, 2019

(30) Foreign Application Priority Data

Oct. 12, 2017 (CN) .......................... 2017 1 0946331

(51) Int. Cl.
| | | |
|---|---|---|
| *G06K 9/00* | (2006.01) | |
| *G06T 7/00* | (2017.01) | |
| *G06T 7/70* | (2017.01) | |
| *G06T 7/11* | (2017.01) | |
| *A61B 3/14* | (2006.01) | |
| *A61B 3/12* | (2006.01) | |
| *A61B 3/00* | (2006.01) | |

(52) U.S. Cl.
CPC .......... *G06T 7/0014* (2013.01); *A61B 3/0025* (2013.01); *A61B 3/12* (2013.01); *A61B 3/14* (2013.01); *G06T 7/11* (2017.01); *G06T 7/70* (2017.01); *G06T 2207/30041* (2013.01); *G06T 2207/30096* (2013.01); *G06T 2207/30242* (2013.01)

(58) Field of Classification Search
CPC . G06T 7/0014; G06T 7/11; G06T 7/70; G06T 2207/30242; G06T 2207/30096; G06T 2207/30041; G06T 7/0012; A61B 3/0025; A61B 3/12; A61B 3/14; G06K 9/0061
USPC ........................................................ 382/128
See application file for complete search history.

(56) References Cited

U.S. PATENT DOCUMENTS

| | | | | |
|---|---|---|---|---|
| 2002/0052551 A1* | 5/2002 | Sinclair | ............... | G06F 19/3418 600/476 |
| 2014/0314288 A1* | 10/2014 | Roychowdhury | .... | G06T 7/0012 382/128 |
| 2015/0104087 A1* | 4/2015 | Katuwal | ................... | G06T 7/11 382/128 |

(Continued)

*Primary Examiner* — Van D Huynh
(74) *Attorney, Agent, or Firm* — Nixon Peabody LLP

(57) ABSTRACT

Embodiments of the present disclosure disclose a method and apparatus for acquiring information. A specific embodiment of the method includes: acquiring a fundus image; introducing the fundus image into a pre-trained disease grading model to obtain disease grading information, the disease grading model being used for extracting characteristic information from a lesion image included in the fundus image, and generating disease grading information based on the extracted characteristic information, the disease grading information including grade information of a disease, a lesion type, a lesion location, and a number of lesions included by the disease; and constructing output information using the disease grading information. This embodiment improves the accuracy of grading information.

13 Claims, 5 Drawing Sheets

(56) References Cited

U.S. PATENT DOCUMENTS

2015/0265144 A1* 9/2015 Burlina .................. A61B 3/12
                                                                         351/206
2018/0315193 A1* 11/2018 Paschalakis ....... G06K 9/00617

* cited by examiner

METHOD AND APPARATUS FOR ACQUIRING INFORMATION

CROSS-REFERENCE TO RELATED APPLICATIONS

This application is related to and claims priority from Chinese Application No. 201710946331.8, filed on Oct. 12, 2017 and entitled "Method and Apparatus for Acquiring Information," the entire disclosure of which is hereby incorporated by reference.

TECHNICAL FIELD

Embodiments of the present disclosure relate to the field of data processing technology, specifically relate to the field of image processing technology, and more specifically relate to a method and apparatus for acquiring information.

BACKGROUND

Diabetic Retinopathy (DR) and Diabetic Macular Edema (DME) are two common eye diseases (hereinafter referred to as diabetic eye diseases) in diabetic patients. The diagnosis of the diabetic eye diseases is mainly based on the doctor's examination of a fundus image of the patient. The fundus image is analyzed according to the grading standards of the DR and the DME, and then the patient's condition is comprehensively evaluated and a treatment plan is determined.

The existing automatic classification and analysis method for diabetic eye diseases can only provide a classification result of the DR and the DME.

SUMMARY

An objective of embodiments of the present disclosure is to propose a method and apparatus for acquiring information, to solve the technical problem mentioned in the foregoing Background section.

In a first aspect, the embodiments of the present disclosure provide a method for acquiring information. The method includes: acquiring a fundus image; introducing the fundus image into a pre-trained disease grading model to obtain disease grading information, the disease grading model being used for extracting characteristic information from a lesion image included in the fundus image, and generating the disease grading information based on the extracted characteristic information, the disease grading information including grade information of a disease, a lesion type, a lesion location, and a number of lesions included by the disease; and constructing output information using the disease grading information.

In some embodiments, the introducing the fundus image into a pre-trained disease grading model to obtain disease grading information includes: extracting location information of a first lesion image from the fundus image, the first lesion image including at least one of: a venous ring image, a vein beading image, or a neovascular image; extracting region information of a second lesion image from the fundus image, the second lesion image including at least one of: a cup optic disc image, a microangioma image, a haemorrhagic spot image, an exudative spot image, or a cotton-wool spot image; and determining the disease grading information of the fundus image, based on the location information and the region information.

In some embodiments, the determining the disease grading information of the fundus image, based on the location information and the region information, includes: performing data processing on a retinopathy image and a macular edema image in the fundus image to obtain initial grading information of retinopathy and initial grading information of macular edema; and establishing a matching relationship respectively between the initial grading information of the retinopathy and the location information and the region information, and between the initial grading information of the macular edema and the location information and the region information, and constructing disease grading information of the retinopathy and disease grading information of the macular edema respectively using the matching relationship.

In some embodiments, the method further includes establishing the disease grading model, and the establishing the disease grading model includes: extracting a reference lesion image from a reference lesion image set, extracting a first reference lesion image from the reference lesion image, and obtaining a lesion detection submodel by training using the first reference lesion image, the first reference lesion image including a first lesion image and location information corresponding to the first lesion image, the first lesion image including at least one of: a venous ring image, a vein beading image, or a neovascular image, wherein the lesion detection submodel is used for recognizing the first lesion image, and outputting the location information corresponding to the first lesion image; extracting a second reference lesion image from the reference lesion image, and obtaining a lesion segmentation submodel by training using the second reference lesion image, the second reference lesion image including a second lesion image and region information corresponding to the second lesion image, the second lesion image including at least one of: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image; and establishing a corresponding relationship respectively between the reference fundus image, the location information and the region information, and grading information of retinopathy, and between the reference fundus image, the location information and the region information, and grading information of macular edema, and obtaining a disease grading submodel by training using the corresponding relationship, wherein the disease grading model is used for outputting the grading information of the retinopathy and/or the grading information of the macular edema based on the corresponding relationship.

In some embodiments, the obtaining a lesion detection submodel by training using the first reference lesion image includes: extracting the first lesion image and the location information corresponding to the first lesion image from the first reference lesion image; establishing a first corresponding relationship between the first lesion image and the location information; and obtaining the lesion detection submodel by training based on the first corresponding relationship using a machine learning method.

In some embodiments, the obtaining a lesion segmentation submodel by training using the second reference lesion image includes: extracting the second lesion image and the region information corresponding to the second lesion image from the second reference lesion image; establishing a second corresponding relationship between the second lesion image and the region information; and obtaining the lesion segmentation submodel by training based on the second corresponding relationship using a machine learning method.

In some embodiments, the obtaining a disease grading submodel by training using the corresponding relationship includes: determining a lesion type using a regional relationship between the region information and the reference fundus image; determining characteristic information corresponding to the lesion type using a location relationship, the characteristic information including at least one of: quantity, position, or area; establishing a third corresponding relationship respectively between the lesion type and the characteristic information and the grading information of the retinopathy, and between the lesion type and the characteristic information and the grading information of the macular edema; and obtaining the disease grading submodel by training based on the third corresponding relationship using a machine learning method.

In a second aspect, the embodiments of the present disclosure provide an apparatus for acquiring information. The apparatus includes: a fundus image acquisition unit, configured to acquire a fundus image; a disease grading information acquisition unit, configured to introduce the fundus image into a pre-trained disease grading model to obtain disease grading information, the disease grading model being used for extracting characteristic information from a lesion image included in the fundus image, and generating the disease grading information based on the extracted characteristic information, the disease grading information including grade information of a disease, a lesion type, a lesion location, and a number of lesions included by the disease; and an output information construction unit, configured to construct output information using the disease grading information.

In some embodiments, the disease grading information acquisition unit includes: a location information acquisition subunit, configured to extract location information of a first lesion image from the fundus image, the first lesion image including at least one of: a venous ring image, a vein beading image, or a neovascular image; an region information acquisition subunit, configured to extract region information of a second lesion image from the fundus image, the second lesion image including at least one of: a cup optic disc image, a microangioma image, a haemorrhagic spot image, an exudative spot image, or a cotton-wool spot image; and a disease grading information acquisition subunit, configured to determine the disease grading information of the fundus image, based on the location information and the region information.

In some embodiments, the disease grading information acquisition subunit includes: an initial grading information acquisition module, configured to perform data processing on a retinopathy image and a macular edema image in the fundus image to obtain initial grading information of retinopathy and initial grading information of macular edema; and a disease grading information acquisition module, configured to establish a matching relationship respectively between the initial grading information of the retinopathy and the location information and the region information, and between the initial grading information of the macular edema and the location information and the region information, and construct disease grading information of the retinopathy and disease grading information of the macular edema respectively using the matching relationship.

In some embodiments, the apparatus further includes a disease grading model establishing unit for establishing the disease grading model, and the disease grading model establishing unit includes: a lesion detection submodel training subunit, configured to extract a reference lesion image from a reference lesion image set, extract a first reference lesion image from the reference lesion image, and obtain a lesion detection submodel by training using the first reference lesion image, the first reference lesion image including a first lesion image and location information corresponding to the first lesion image, the first lesion image including at least one of: a venous ring image, a vein beading image, or a neovascular image, wherein the lesion detection submodel is used for recognizing the first lesion image, and outputting the location information corresponding to the first lesion image; a lesion segmentation submodel training subunit, configured to extract a second reference lesion image from the reference lesion image, and obtain a lesion segmentation submodel by training using the second reference lesion image, the second reference lesion image including a second lesion image and region information corresponding to the second lesion image, the second lesion image including at least one of: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image; and a disease grading submodel training subunit, configured to establish a corresponding relationship respectively between the reference fundus image, the location information and the region information, and grading information of retinopathy, and between the reference fundus image, the location information and the region information, and grading information of macular edema, and obtain a disease grading submodel by training using the corresponding relationship, wherein the disease grading model is used for outputting the grading information of the retinopathy and/or the grading information of the macular edema based on the corresponding relationship.

In some embodiments, the lesion detection submodel training subunit includes: a first information extraction module, configured to extract the first lesion image and the location information corresponding to the first lesion image from the first reference lesion image; a first corresponding relationship establishing module, configured to establish a first corresponding relationship between the first lesion image and the location information; and a lesion detection submodel training module, configured to obtain the lesion detection submodel by training based on the first corresponding relationship using a machine learning method.

In some embodiments, the lesion segmentation submodel training subunit includes: a second information extraction module, configured to extract the second lesion image and the region information corresponding to the second lesion image from the second reference lesion image; a second corresponding relationship establishing module, configured to establish a second corresponding relationship between the second lesion image and the region information; and a lesion segmentation submodel training module, configured to obtain the lesion segmentation submodel by training based on the second corresponding relationship using a machine learning method.

In some embodiments, the disease grading submodel training subunit includes: a lesion type determination module, configured to determine a lesion type using a regional relationship between the region information and the reference fundus image; a characteristic information determination module, configured to determine characteristic information corresponding to the lesion type using a location relationship, the characteristic information including at least one of: quantity, position, or area; a third corresponding relationship establishing module, configured to establish a third corresponding relationship respectively between the lesion type and the characteristic information and the grading information of the retinopathy, and between the lesion type and the characteristic information and the grading information of the macular edema; and a disease grading submodel training module, configured to obtain the disease grading submodel by training based on the third corresponding relationship using a machine learning method.

In a third aspect, the embodiments of the present disclosure provide a server, including: one or more processors; and a storage apparatus, for storing one or more programs, the one or more programs, when executed by the one or more processors, cause the one or more processors to implement the method for acquiring information according to the first aspect.

In a fourth aspect, the embodiments of the present disclosure provide a computer readable storage medium, storing a computer program thereon, the program, when executed by a processor, implements the method for acquiring information according to the first aspect.

The method and apparatus for acquiring information provided by the embodiments of the present disclosure may simultaneously acquire grading information of retinopathy and grading information of macular edema from a fundus image, and information such as the lesion type, the number of lesions, the lesion location as specifically included by the retinopathy and macular edema, which improves the accuracy of grading information.

BRIEF DESCRIPTION OF THE DRAWINGS

After reading detailed descriptions of non-limiting embodiments with reference to the following accompanying drawings, other features, objectives and advantages of the present disclosure will become more apparent.

DETAILED DESCRIPTION OF EMBODIMENTS

The present disclosure will be further described below in detail in combination with the accompanying drawings and the embodiments. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should be noted that the embodiments in the present disclosure and the features in the embodiments may be combined with each other on a non-conflict basis. The present disclosure will be described below in detail with reference to the accompanying drawings and in combination with the embodiments.

Figure 1:
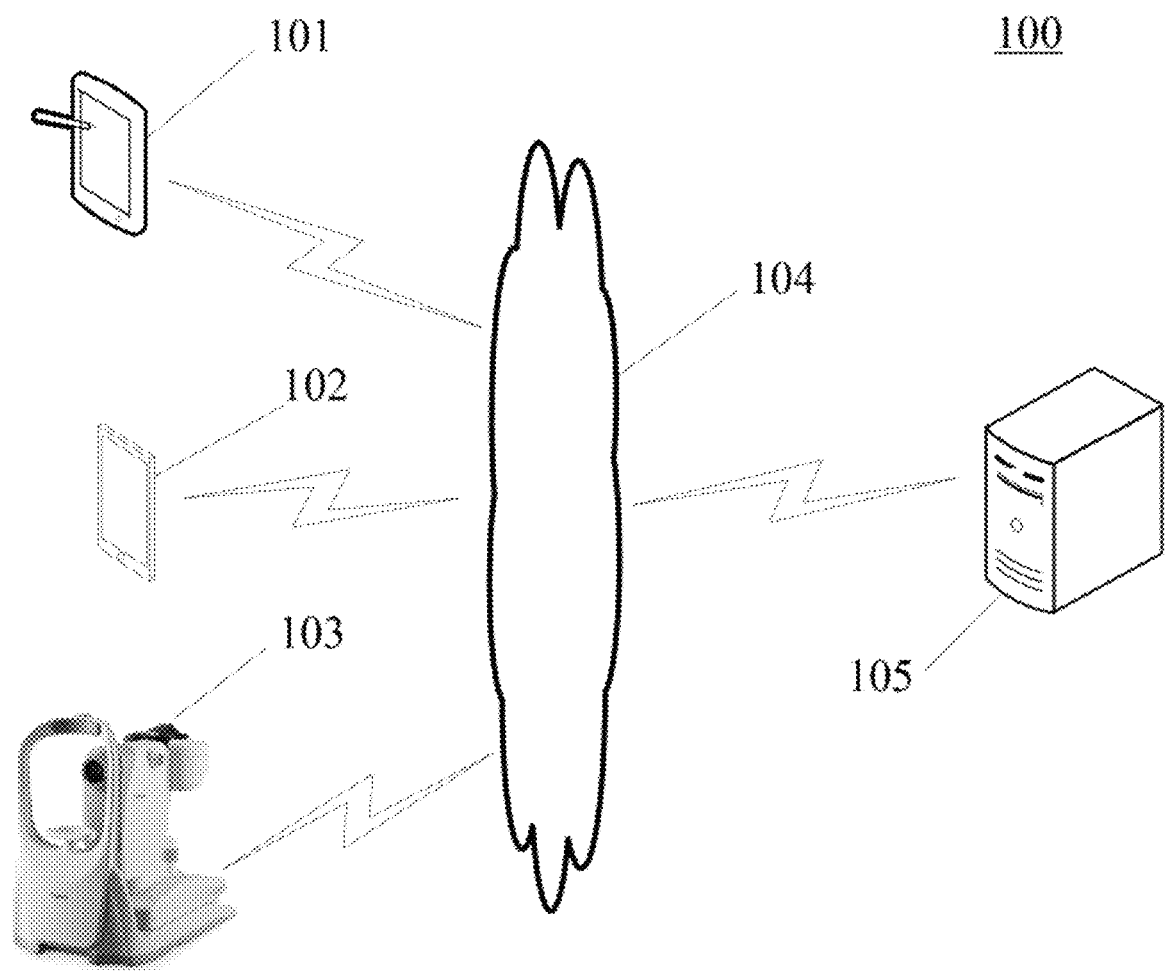
FIG. 1 is an architecture diagram of an exemplary system in which the present disclosure may be implemented.

FIG. 1 shows an architecture of an exemplary system 100 which may be used by a method for acquiring information or an apparatus for acquiring information according to the embodiments of the present disclosure.

As shown in FIG. 1, the system architecture 100 may include terminal devices 101, 102 and 103, a network 104, and a server 105. The network 104 serves as a medium providing a communication link between the terminal devices 101, 102 and 103, and the server 105. The network 104 may include various types of connections, such as wired or wireless transmission links, or optical fibers.

The user may use the terminal devices 101, 102 and 103 to interact with the server 105 through the network 104, to receive or transmit messages. Various image applications, such as fundus image acquisition applications, image edition applications and information sending applications may be installed on the terminal devices 101, 102 and 103.

The terminal devices 101, 102 and 103 may be various electronic devices having display screens and supporting image display, including but not limited to, smart phones, tablet computers, laptop computers, desktop computers and digital fundus cameras.

The server 105 may be a server providing various services, for example, a server that performs image processing on the fundus image sent by the terminal devices 101, 102 or 103 to obtain diabetes grading information. The server may perform analyzing and processing on data such as received fundus image, to obtain grading information of diabetes retinopathy and grading information of macular edema corresponding to the fundus image, and information such as the lesion type, the lesion location, the number of lesions, the lesion area as specifically included by the retinopathy and macular edema, which improves the accuracy and interpretability of grading information of retinopathy and grading information of macular edema.

It should be noted that the method for acquiring information according to the embodiments of the present disclosure is generally executed by the server 105. Accordingly, an apparatus for acquiring information is generally installed on the server 105.

It should be appreciated that the numbers of the terminal devices, the networks, and the servers in FIG. 1 are merely illustrative. Any number of terminal devices, networks, and servers may be provided based on the actual requirements.

Figure 2:
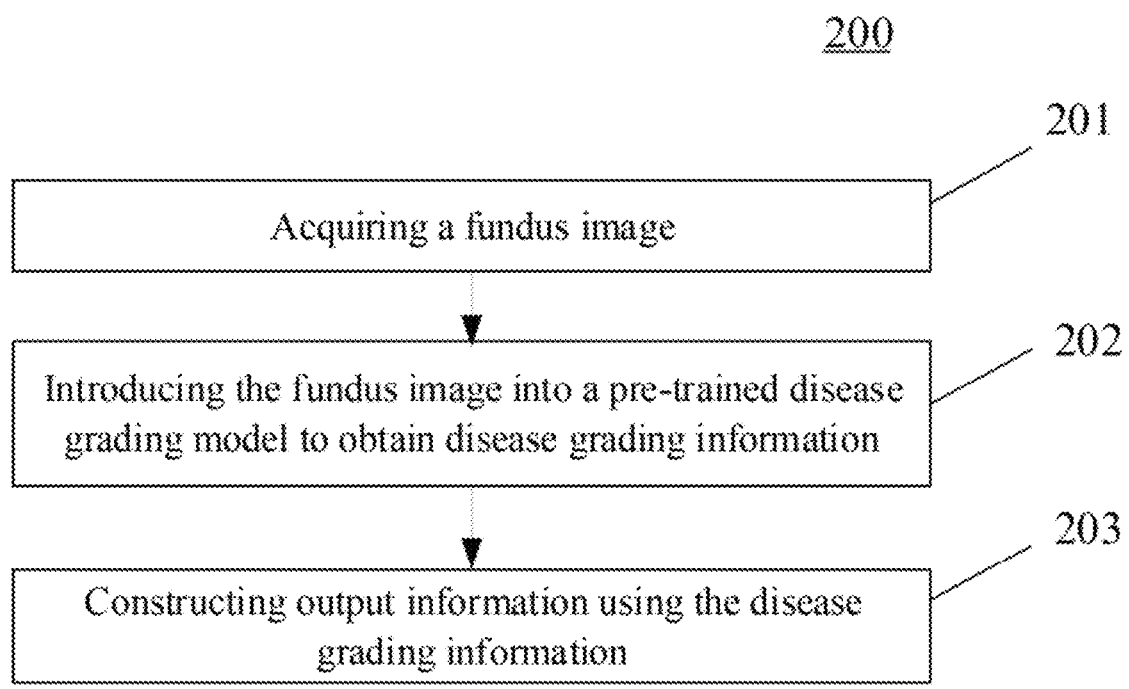
FIG. 2 is a flowchart of an embodiment of a method for acquiring information according to the present disclosure.

With further reference to FIG. 2, a flow 200 of an embodiment of the method for acquiring information according to the present disclosure is illustrated. The method for acquiring information includes the following steps.

Step 201, acquiring a fundus image.

In the present embodiment, the electronic device (e.g., the server 105 as shown in FIG. 1) on which the method for acquiring information is performed may acquire a fundus image through a wired connection or a wireless connection from the terminal devices 101, 102 or 103. It should be noted that the wireless connection may include, but is not limited to, 3G/4G connection, WiFi connection, Bluetooth connection, WiMAX connection, Zigbee connection, UWB (ultra wideband) connection, and other wireless connections already known by now or to be developed in the future.

Typically, the fundus image may be directly acquired by a terminal device (for example, a digital fundus camera) and sent to the server 105. Alternatively, the fundus image may also be indirectly acquired by the terminal device from other devices and then sent to the server 105. The fundus image contains a lesion image of retinopathy and a lesion image of macular edema that may be related to diabetes.

Step 202, introducing the fundus image into a pre-trained disease grading model to obtain disease grading information.

After acquiring the fundus image, the fundus image may be introduced into a pre-trained disease grading model. The disease grading model is used for extracting characteristic information from a lesion image included in the fundus image, and generating disease grading information based on the extracted characteristic information. The disease grading information may include grade information of a disease, a lesion type, a lesion location, and a number of lesions included by the disease.

When the fundus image contains a lesion image of retinopathy and/or a lesion image of macular edema, the obtained disease grading information includes grade information of retinopathy and/or grade information of macular edema, and information such as specific lesion type, lesion location, and number of lesions included by retinopathy and/or macular edema. When the fundus image does not contain the lesion image of retinopathy and/or the lesion image of macular edema, the obtained disease grading information may not contain grade information of retinopathy and/or grade information of macular edema. Here, the grade information of retinopathy may include grades 1 to 4; and the grade information of macular edema may include grades 1 to 3.

In some alternative implementations of the present embodiment, the introducing the fundus image into a pre-trained disease grading model to obtain disease grading information may include the following steps.

The first step: extracting location information of a first lesion image from the fundus image.

The fundus image may include various types of lesion images, and the first lesion image may be extracted from the fundus image based on the characteristics of the various types of lesion images, and location information corresponding to the first lesion image may be obtained at the same time. Here, the first lesion image includes at least one of the following: a venous ring image, a vein beading image, or a neovascular image.

The second step: extracting region information of a second lesion image from the fundus image.

Some lesions in the fundus image are regional, so that the lesions may be recognized in a setting area of the fundus image. After a lesion is recognized, the area in which the lesion is located is determined as the region information corresponding to the second lesion image. Here, the second lesion image includes at least one of the following: a cup optic disc image, a microangioma image, a haemorrhagic spot image, an exudative spot image, or a cotton-wool spot image. Alternatively, the region information may be identified using different colors.

The third step: determining the disease grading information of the fundus image, based on the location information and the region information.

After obtaining the location information and the region information, the lesion corresponding to the location information and the region information is comprehensively analyzed to obtain the disease grading information of the fundus image.

In some alternative implementations of the present embodiment, the determining the disease grading information of the fundus image, based on the location information and the region information may include the following steps.

The first step: performing data processing on a retinopathy image and a macular edema image in the fundus image to obtain initial grading information of retinopathy and initial grading information of macular edema.

The disease grading model may process a retinopathy image and a macular edema image in the fundus image to obtain initial grading information of retinopathy and initial grading information of macular edema. The initial grading information may contain the lesion type.

The second step: establishing a matching relationship respectively between the initial grading information of the retinopathy and the location information and the region information, and between the initial grading information of the macular edema and the location information and the region information, and constructing disease grading information of the retinopathy and disease grading information of the macular edema respectively through the matching relationship.

The initial grading information cannot provide detailed information about the lesion, but the location information and the region information described above may provide detailed data on the lesion. The location information and the region information may be statisticised based on the lesion type. The grading information of retinopathy and the grading information of macular edema may be obtained based on the initial grading information and the location information and the region information. Here, the grading information includes information on the disease type (retinopathy or macular edema), the disease grade, the lesion location, and the number of lesions included by the disease.

In some alternative implementations of the present embodiment, the method may further include establishing the disease grading model, and the establishing the disease grading model may include the following steps:

The first step: extracting a reference lesion image from a reference lesion image set, extracting a first reference lesion image from the reference lesion image, and obtaining a lesion detection submodel by training using the first reference lesion image.

To train the disease grading model, a reference lesion image may be extracted from a reference lesion image set. The reference lesion image contains grading information of retinopathy and grading information of macular edema, as well as location information and region information of various lesions of the retinopathy and macular edema. First, the first reference lesion image may be extracted from the reference lesion image. The first reference lesion image includes the first lesion image and location information corresponding to the first lesion image. Then, the lesion detection submodel is obtained by training based on the first lesion image and the location information corresponding to the first lesion image. The first lesion image includes at least one of the following: a venous ring image, a vein beading image, or a neovascular image. The lesion detection submodel is used for recognizing the first lesion image and outputting the location information corresponding to the first lesion image. The location information may be described by text, or may be described by coordinates, and may also be described by other means, detailed description thereof will be omitted.

The second step: extracting a second reference lesion image from the reference lesion image, and obtaining a lesion segmentation submodel by training using the second reference lesion image.

The second reference lesion image is extracted from the reference lesion image. The second reference lesion image includes a second lesion image and region information corresponding to the second lesion image. The second lesion image includes at least one of the following: a cup optic disc image, a microangioma image, a haemorrhagic spot image, an exudative spot image, or a cotton-wool spot image. The region information is used for describing a certain area in which the lesion is located in the fundus image. The area may be identified using colors. Then, the lesion segmentation submodel is obtained by training based on the second lesion image and the region information corresponding to the second lesion image. The lesion segmentation submodel is used for recognizing the second lesion image and outputting the region information corresponding to the second lesion image.

The third step: establishing a corresponding relationship respectively between the reference fundus image, the location information and the region information, and grading information of retinopathy, and between the reference fundus image, the location information and the region information, and grading information of macular edema, and obtaining a disease grading submodel by training using the corresponding relationship.

The reference fundus image contains the grading information of the retinopathy and the grading information of the macular edema, as well as various lesions, the location information of the lesions, and the region information of the lesions of the retinopathy and macular edema. The disease grading submodel may be obtained by training through establishing a corresponding relationship respectively between the reference fundus image, the location information and the region information, and the grading information of the retinopathy, and between the reference fundus image, the location information and the region information, and the grading information of the macular edema by the neural network. The disease grading model is used for outputting the grading information of retinopathy and/or the grading information of macular edema based on the corresponding relationship.

In some alternative implementations of the present embodiment, the obtaining a lesion detection submodel by training using the first reference lesion image may include the following steps.

The first step: extracting the first lesion image and the location information corresponding to the first lesion image from the first reference lesion image.

After acquiring the first reference lesion image, image processing is performed on the first reference lesion image, then the first lesion image and the location information corresponding to the first lesion image in the first reference lesion image may be obtained.

The second step: establishing a first corresponding relationship between the first lesion image and the location information.

Different lesions in the fundus image usually appear in specific locations, that is, the lesion is regional to some extent. Based on the location information, the first corresponding relationship between the first lesion image and the location information may be established.

The third step: obtaining the lesion detection submodel by training based on the first corresponding relationship using a machine learning method.

The server 105 may use the lesion image as an input, and use the location information as an output to obtain the lesion detection submodel by training using the machine learning method. Specifically, the server 105 may use the lesion image as an input of the model, and use the location information as the corresponding output of the model using the Faster R-CNN network, the Mask R-CNN network, the Single Shot Detector (SSD) network or the RetinaNet network, and train the model to obtain the lesion detection submodel using the machine learning method.

In some alternative implementations of the present embodiment, the obtaining a lesion segmentation submodel by training using the second reference lesion image may include the following steps.

The first step: extracting the second lesion image and the region information corresponding to the second lesion image from the second reference lesion image.

After acquiring the second reference lesion image, image processing is performed on the second reference lesion image, then the second lesion image and the region information corresponding to the second lesion image may be extracted from the second reference lesion image.

The second step: establishing a second corresponding relationship between the second lesion image and the region information.

In the fundus image, different areas of the second lesion image are annotated using different colors or other means. Therefore, the second corresponding relationship may be established based on the second lesion image and the region information.

The third step: obtaining the lesion segmentation submodel by training based on the second corresponding relationship using a machine learning method.

The server 105 may use the lesion image as an input, and use the region information as an output to obtain the lesion segmentation submodel by training using the machine learning method. Specifically, the server 105 may use the lesion image as an input of the model, and use the region information as the corresponding output of the model using the Fully Convolutional Network (FCN) or the Dilated Convolution network, and train the model to obtain the lesion segmentation submodel using the machine learning method.

In some alternative implementations of the present embodiment, the obtaining a disease grading submodel by training using the corresponding relationship may include the following steps.

The first step: determining a lesion type using a regional relationship between the region information and the reference fundus image.

The region information has a corresponding relationship with the lesion image, and different lesion images correspond to different region information. Therefore, the lesion type may be determined using the regional relationship between the region information and the reference fundus image.

The second step: determining characteristic information of corresponding lesion type using a location relationship.

The location information also has a corresponding relationship with the lesion, and the corresponding lesion type may be found through the location information, and then the characteristic information of the lesion type is determined from the lesion image corresponding to the lesion type. The characteristic information includes at least one of the following: quantity, location, or area.

The third step: establishing a third corresponding relationship respectively between the lesion type and the characteristic information and the grading information of the retinopathy, and between the lesion type and the characteristic information and the grading information of the macular edema.

Retinopathy and macular edema contain multiple types of lesions, each lesion has its own characteristic information. Moreover, the grading information of retinopathy and the grading information of macular edema may be determined using the multiple types of lesions and the characteristic information of corresponding lesions.

Therefore, the third corresponding relationship respectively between the lesion type and the characteristic information and the grading information of the retinopathy, and between the lesion type and the characteristic information and the grading information of the macular edema may be established through the neural network.

The fourth step: obtaining the disease grading submodel by training based on the third corresponding relationship using a machine learning method.

The server 105 may use the lesion type and the characteristic information as an input, and use the grading information of retinopathy and the grading information of macular edema as an output to obtain the disease grading submodel by training using the machine learning method. Specifically, the server 105 may use the lesion type and the characteristic information as an input of the model, and use the grading information of retinopathy and the grading information of macular edema as the corresponding output of the model using a model of the Deep Residual Networks (ResNet for short) for grading, and train the model to obtain the disease grading submodel using the machine learning method.

It should be noted that the disease grading model may be trained using a deep learning algorithm or other existing or future possible algorithms. The present embodiment does not limit the algorithm for training the disease grading model.

Step 203, constructing output information based on the disease grading information.

After obtaining the disease grading information, the output information may be constructed using the disease grading information as needed.

Figure 3:
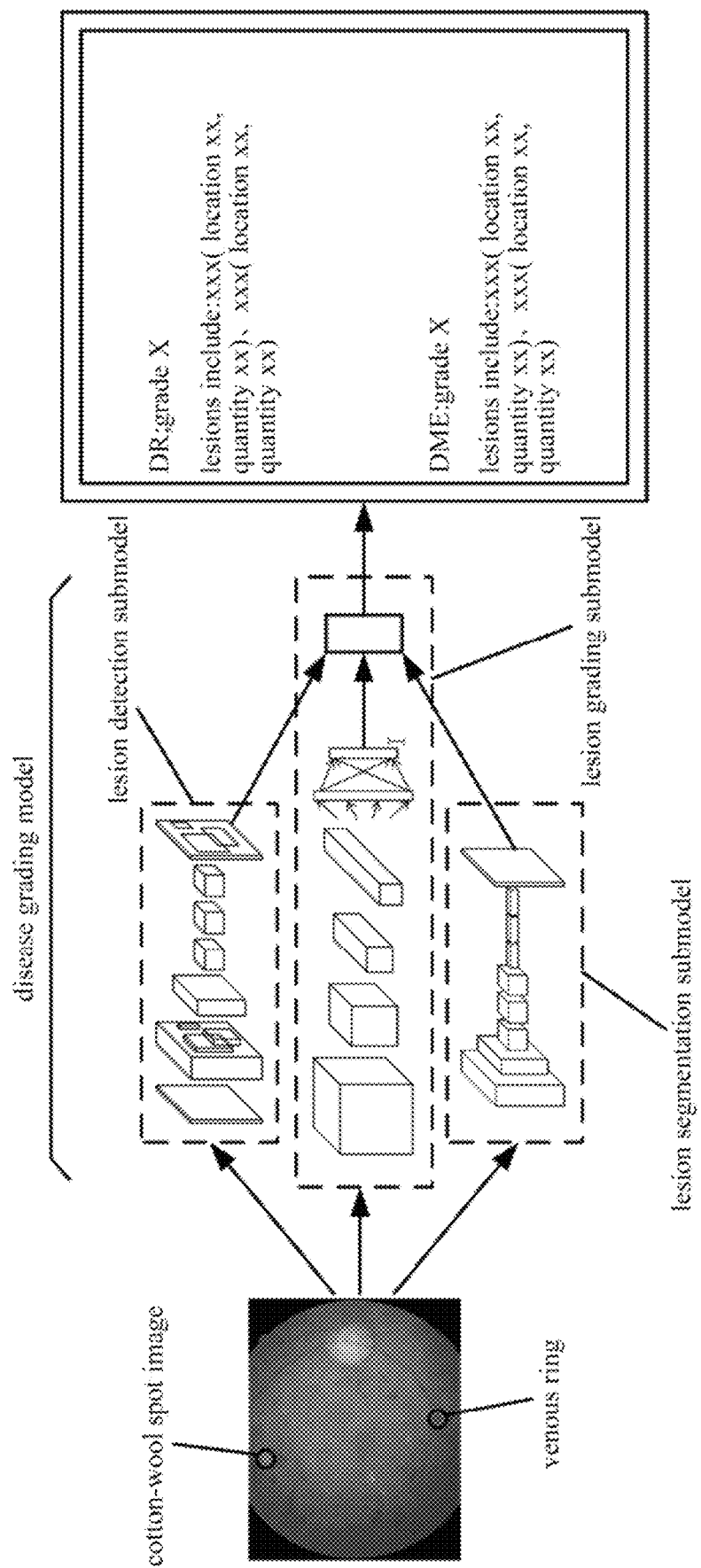
FIG. 3 is a schematic diagram of an application scenario of the method for acquiring information according to the present disclosure.

With further reference to FIG. 3, a schematic diagram of an application scenario of the method for acquiring information according to the present embodiment is illustrated. In the application scenario of FIG. 3, the acquired fundus image contains a lesion image of retinopathy (e.g., the venous ring as shown in FIG. 3) and a lesion image of macular edema (e.g., the cotton-wool spot as shown in FIG. 3). The fundus image is inputted into the lesion detection submodel, the lesion grading submodel, and the lesion segmentation submodel respectively, and the output of the lesion detection submodel and the output of the lesion segmentation submodel are inputted to an output layer of the lesion grading submodel, and finally the grading information is obtained.

The method provided by the embodiments of the present disclosure may simultaneously acquire grading information of retinopathy and grading information of macular edema from a fundus image, and information such as the lesion type, the number of lesions, the lesion location as specifically included by the retinopathy and macular edema, which improves the accuracy and interpretability of grading information.

Figure 4:
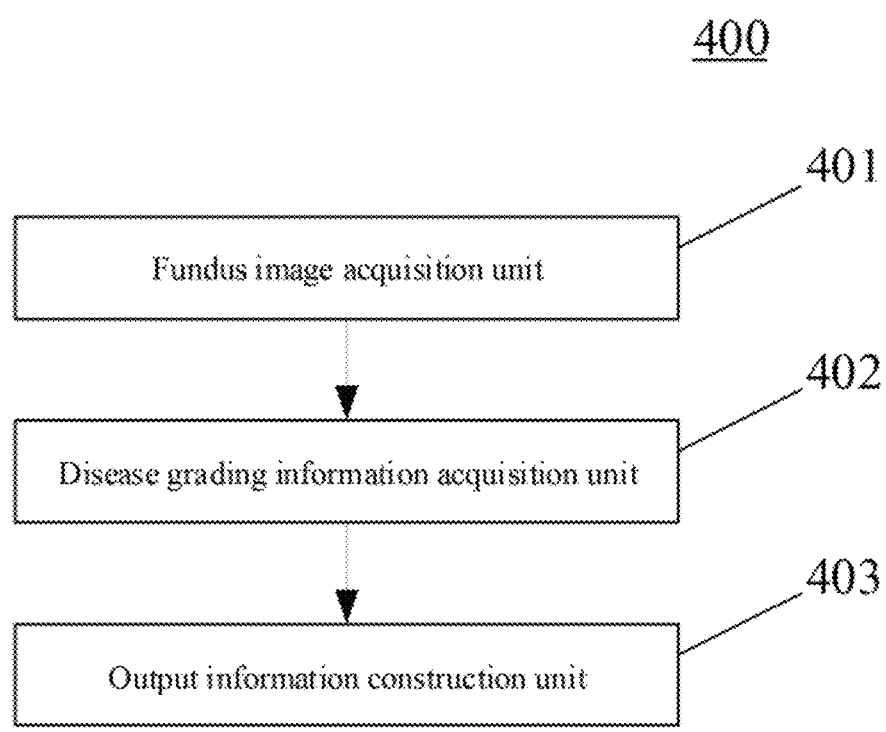
FIG. 4 is a schematic structural diagram of an embodiment of an apparatus for acquiring information according to the present disclosure.

With further reference to FIG. 4, as an implementation to the method shown in the above figures, the present disclosure provides an embodiment of an apparatus for acquiring information. The apparatus embodiment corresponds to the method embodiment shown in FIG. 2, and the apparatus may specifically be applied to various electronic devices.

As shown in FIG. 4, the apparatus 400 for acquiring information of the present embodiment may include: a fundus image acquisition unit 401, a disease grading information acquisition unit 402 and an output information construction unit 403. The fundus image acquisition unit 401 is configured to acquire a fundus image. The disease grading information acquisition unit 402 is configured to introduce the fundus image into a pre-trained disease grading model to obtain disease grading information, the disease grading model being used for extracting characteristic information from a lesion image included in the fundus image, and generating the disease grading information based on the extracted characteristic information, the disease grading information including grade information of a disease, a lesion type, a lesion location, and a number of lesions included by the disease. The output information construction unit 403 is configured to construct output information using the disease grading information.

In some alternative implementations of the present embodiment, the disease grading information acquisition unit 402 may include: a location information acquisition subunit (not shown in the figure), an region information acquisition subunit (not shown in the figure) and a disease grading information acquisition subunit (not shown in the figure). The location information acquisition subunit is configured to extract location information of a first lesion image from the fundus image, the first lesion image including at least one of the following: a venous ring image, a vein beading image, or a neovascular image. The region information acquisition subunit is configured to extract region information of a second lesion image from the fundus image, the second lesion image including at least one of the following: a cup optic disc image, a microangioma image, a haemorrhagic spot image, an exudative spot image, or a cotton-wool spot image. The disease grading information acquisition subunit is configured to determine the disease grading information of the fundus image, based on the location information and the region information.

In some alternative implementations of the present embodiment, the disease grading information acquisition subunit may include: an initial grading information acquisition module (not shown in the figure) and a disease grading information acquisition module (not shown in the figure). The initial grading information acquisition module is configured to perform data processing on a retinopathy image and a macular edema image in the fundus image to obtain initial grading information of retinopathy and initial grading information of macular edema. The disease grading information acquisition module is configured to establish a matching relationship respectively between the initial grading information of the retinopathy and the location information and the region information, and between the initial grading information of the macular edema and the location information and the region information, and construct disease grading information of the retinopathy and disease grading information of the macular edema respectively using the matching relationship.

In some alternative implementations of the present embodiment, the apparatus of the present embodiment further includes a disease grading model establishing unit (not shown in the figure) for establishing the disease grading model, and the disease grading model establishing unit may include: a lesion detection submodel training subunit (not shown in the figure), a lesion segmentation submodel training subunit (not shown in the figure) and a disease grading submodel training subunit (not shown in the figure). The lesion detection submodel training subunit is configured to extract a reference lesion image from a reference lesion image set, extract a first reference lesion image from the reference lesion image, and obtain a lesion detection submodel by training using the first reference lesion image, the first reference lesion image including a first lesion image and location information corresponding to the first lesion image, the first lesion image including at least one of the following: a venous ring image, a vein beading image, or a neovascular image, wherein the lesion detection submodel is used for recognizing the first lesion image, and outputting the location information corresponding to the first lesion image. The lesion segmentation submodel training subunit is configured to extract a second reference lesion image from the reference lesion image, and obtain a lesion segmentation submodel by training using the second reference lesion image, the second reference lesion image including a second lesion image and region information corresponding to the second lesion image, the second lesion image including at least one of the following: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image. The disease grading submodel training subunit is configured to establish a corresponding relationship respectively between the reference fundus image, the location information and the region information, and grading information of retinopathy, and between the reference fundus image, the location information and the region information, and grading information of macular edema, and obtain a disease grading submodel by training using the corresponding relationship, wherein the disease grading model is used for outputting the grading information of the retinopathy and/or the grading information of the macular edema based on the corresponding relationship.

In some alternative implementations of the present embodiment, the lesion detection submodel training subunit may include: a first information extraction module (not shown in the figure), a first corresponding relationship establishing module (not shown in the figure) and a lesion detection submodel training module (not shown in the figure). The first information extraction module is configured to extract the first lesion image and the location information corresponding to the first lesion image from the first reference lesion image. The first corresponding relationship establishing module is configured to establish a first corresponding relationship between the first lesion image and the location information. The lesion detection submodel training module is configured to obtain the lesion detection submodel by training based on the first corresponding relationship using a machine learning method.

In some alternative implementations of the present embodiment, the lesion segmentation submodel training subunit may include: a second information extraction module (not shown in the figure), a second corresponding relationship establishing module (not shown in the figure) and a lesion segmentation submodel training module (not shown in the figure). The second information extraction module is configured to extract the second lesion image and the region information corresponding to the second lesion image from the second reference lesion image. The second corresponding relationship establishing module is configured to establish a second corresponding relationship between the second lesion image and the region information. The lesion segmentation submodel training module is configured to obtain the lesion segmentation submodel by training based on the second corresponding relationship using a machine learning method.

In some alternative implementations of the present embodiment, the disease grading submodel training subunit may include: a lesion type determination module (not shown in the figure), a characteristic information determination module (not shown in the figure), a third corresponding relationship establishing module (not shown in the figure) and a disease grading submodel training module (not shown in the figure). The lesion type determination module is configured to determine a lesion type using a regional relationship between the region information and the reference fundus image. The characteristic information determination module is configured to determine characteristic information corresponding to the lesion type using a location relationship, the characteristic information including at least one of the following: quantity, position, or area. The third corresponding relationship establishing module is configured to establish a third corresponding relationship respectively between the lesion type and the characteristic information and the grading information of the retinopathy, and between the lesion type and the characteristic information and the grading information of the macular edema. The disease grading submodel training module is configured to obtain the disease grading submodel by training based on the third corresponding relationship using a machine learning method.

The present embodiment also provides a server, including: one or more processors; and a storage apparatus, for storing one or more programs, the one or more programs, when executed by the one or more processors, cause the one or more processors to implement the method for acquiring information.

The present embodiment also provides a computer readable storage medium, storing a computer program thereon, the program, when executed by a processor, implements the method for acquiring information.

Figure 5:
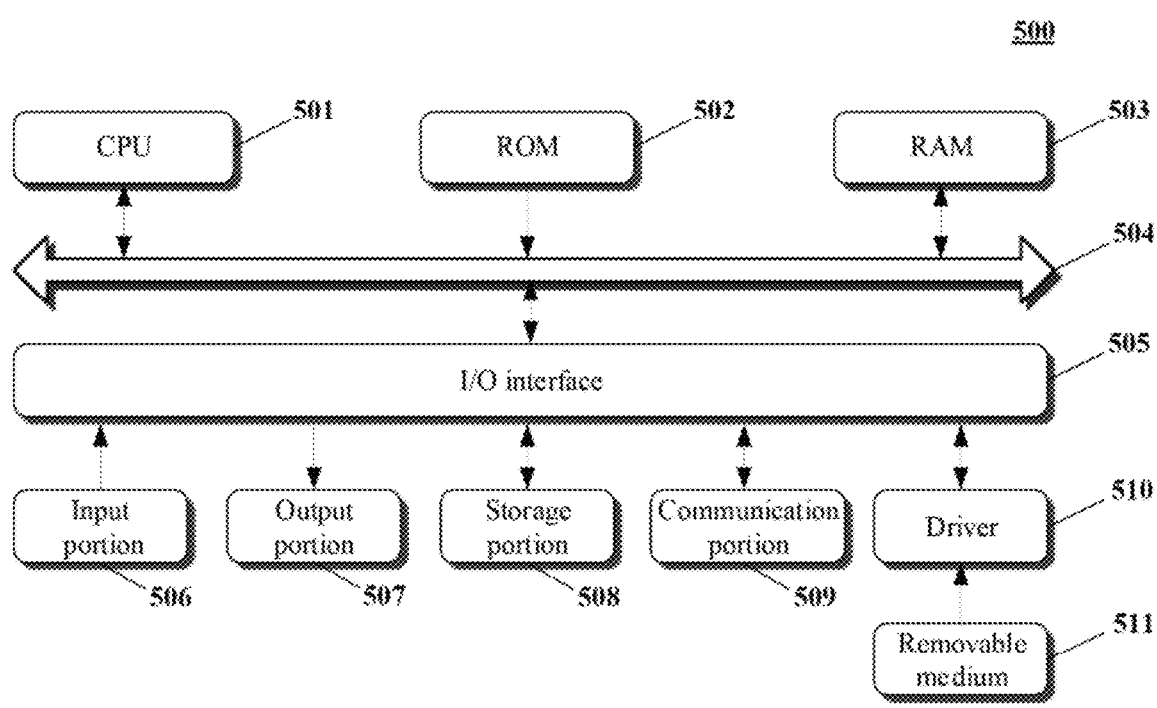
FIG. 5 is a schematic structural diagram of a computer system adapted to implement a server of embodiments of the present disclosure.

Referring to FIG. 5, which is a schematic structural diagram of a computer system 500 adapted to implement a server according to embodiments of the present disclosure. The server shown in FIG. 5 is merely an example, and should not bring any limitations to the functions and the scope of use of the embodiments of the present disclosure.

As shown in FIG. 5, the computer system 500 includes a central processing unit (CPU) 501, which may execute various appropriate actions and processes in accordance with a program stored in a read-only memory (ROM) 502 or a program loaded into a random access memory (RAM) 503 from a storage portion 508. The RAM 503 also stores various programs and data required by operations of the system 500. The CPU 501, the ROM 502 and the RAM 503 are connected to each other through a bus 504. An input/output (I/O) interface 505 is also connected to the bus 504.

The following components are connected to the I/O interface 505: an input portion 506 including a keyboard, a mouse etc.; an output portion 507 comprising a cathode ray tube (CRT), a liquid crystal display device (LCD), a speaker etc.; a storage portion 508 including a hard disk and the like; and a communication portion 509 comprising a network interface card, such as a LAN card and a modem. The communication portion 509 performs communication processes via a network, such as the Internet. A driver 510 is also connected to the I/O interface 505 as required. A removable medium 511, such as a magnetic disk, an optical disk, a magneto-optical disk, and a semiconductor memory, may be installed on the driver 510, to facilitate the retrieval of a computer program from the removable medium 511, and the installation thereof on the storage portion 508 as needed.

In particular, according to embodiments of the present disclosure, the process described above with reference to the flow chart may be implemented in a computer software program. For example, an embodiment of the present disclosure includes a computer program product, which comprises a computer program that is tangibly embedded in a machine-readable medium. The computer program comprises program codes for executing the method as illustrated in the flow chart. In such an embodiment, the computer program may be downloaded and installed from a network via the communication portion 509, and/or may be installed from the removable media 511. The computer program, when executed by the central processing unit (CPU) 501, implements the above mentioned functionalities as defined by the methods of the present disclosure.

It should be noted that the computer readable medium in the present disclosure may be computer readable signal medium or computer readable storage medium or any combination of the above two. An example of the computer readable storage medium may include, but not limited to: electric, magnetic, optical, electromagnetic, infrared, or semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fiber, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. In the present disclosure, the computer readable signal medium may include data signal in the base band or propagating as parts of a carrier, in which computer readable program codes are carried. The propagating signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units involved in the embodiments of the present disclosure may be implemented by means of software or hardware. The described units may also be provided in a processor, for example, described as: a processor, comprising a fundus image acquisition unit, a disease grading information acquisition unit and an output information construction unit where the names of these units do not in some cases constitute a limitation to such units themselves. For example, the output information construction unit may also be described as "a unit for constructing output information."

In another aspect, the present disclosure further provides a computer-readable storage medium. The computer-readable storage medium may be the computer storage medium included in the apparatus in the above described embodiments, or a stand-alone computer-readable storage medium not assembled into the apparatus. The computer-readable storage medium stores one or more programs. The one or more programs, when executed by the apparatus, cause the apparatus to: acquiring a fundus image; introducing the fundus image into a pre-trained disease grading model to obtain disease grading information, the disease grading model being used for extracting characteristic information from a lesion image contained in the fundus image, and generating the disease grading information based on the extracted characteristic information, the disease grading information comprising grade information of a disease, a lesion type, a lesion location, and a number of lesions included by the disease; and constructing output information using the disease grading information.

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the disclosure. Technical schemes formed by the above-described features being interchanged with, but not limited to, technical features with similar functions disclosed in the present disclosure are examples.

What is claimed is:

1. A method for acquiring information, the method comprising:
   acquiring a fundus image;
   introducing the fundus image into a pre-trained disease grading model to obtain disease grading information, the disease grading model being used for extracting characteristic information from a lesion image contained in the fundus image, and generating the disease grading information based on the extracted characteristic information, the disease grading information comprising grade information of a disease, a lesion type, a lesion location, and a number of lesions included by the disease; and
   constructing output information using the disease grading information;
   wherein the method further comprises establishing the disease grading model, and the establishing the disease grading model comprises:
   extracting a reference lesion image from a reference lesion image set, extracting a first reference lesion image from the reference lesion image, and obtaining a lesion detection submodel by training using the first reference lesion image, the first reference lesion image comprising a first lesion image and location information corresponding to the first lesion image, the first lesion image comprising at least one of: a venous ring image, a vein beading image, or a neovascular image, wherein the lesion detection submodel is used for recognizing the first lesion image, and outputting the location information corresponding to the first lesion image;

extracting a second reference lesion image from the reference lesion image, and obtaining a lesion segmentation submodel by training using the second reference lesion image, the second reference lesion image comprising a second lesion image and region information corresponding to the second lesion image, the second lesion image comprising at least one of: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image; and establishing a corresponding relationship respectively between the reference fundus image, the location information and the region information, and grading information of retinopathy, and between the reference fundus image, the location information and the region information, and grading information of macular edema, and obtaining a disease grading submodel by training using the corresponding relationship, wherein the disease grading model is used for outputting the grading information of the retinopathy and/or the grading information of the macular edema based on the corresponding relationship.

2. The method according to claim 1, wherein, the introducing the fundus image into a pre-trained disease grading model to obtain disease grading information comprises:

extracting location information of a first lesion image from the fundus image, the first lesion image comprising at least one of: a venous ring image, a vein beading image, or a neovascular image;

extracting region information of a second lesion image from the fundus image, the second lesion image comprising at least one of: a cup optic disc image, a microangioma image, a haemorrhagic spot image, an exudative spot image, or a cotton-wool spot image; and determining the disease grading information of the fundus image, based on the location information and the region information.

3. The method according to claim 2, wherein, the determining the disease grading information of the fundus image, based on the location information and the region information, comprises:

performing data processing on a retinopathy image and a macular edema image in the fundus image to obtain initial grading information of retinopathy and initial grading information of macular edema; and establishing a matching relationship respectively between the initial grading information of the retinopathy and the location information and the region information, and between the initial grading information of the macular edema and the location information and the region information, and constructing disease grading information of the retinopathy and disease grading information of the macular edema respectively using the matching relationship.

4. The method according to claim 1, wherein, the obtaining a lesion detection submodel by training using the first reference lesion image comprises:

extracting the first lesion image and the location information corresponding to the first lesion image from the first reference lesion image;

establishing a first corresponding relationship between the first lesion image and the location information; and obtaining the lesion detection submodel by training based on the first corresponding relationship using a machine learning method.

5. The method according to claim 1, wherein, the obtaining a lesion segmentation submodel by training using the second reference lesion image comprises:

extracting the second lesion image and the region information corresponding to the second lesion image from the second reference lesion image;

establishing a second corresponding relationship between the second lesion image and the region information; and obtaining the lesion segmentation submodel by training based on the second corresponding relationship using a machine learning method.

6. The method according to claim 1, wherein, the obtaining a disease grading submodel by training using the corresponding relationship comprises:

determining a lesion type using a regional relationship between the region information and the reference fundus image;

determining characteristic information corresponding to the lesion type using a location relationship, the characteristic information comprising at least one of: quantity, position, or area;

establishing a third corresponding relationship respectively between the lesion type and the characteristic information and the grading information of the retinopathy, and between the lesion type and the characteristic information and the grading information of the macular edema; and obtaining the disease grading submodel by training based on the third corresponding relationship using a machine learning method.

7. An apparatus for acquiring information, the apparatus comprising:

at least one processor; and a memory storing instructions, the instructions when executed by the at least one processor, cause the at least one processor to perform operations, the operations comprising:

acquiring a fundus image;

introducing the fundus image into a pre-trained disease grading model to obtain disease grading information, the disease grading model being used for extracting characteristic information from a lesion image included in the fundus image, and generating the disease grading information based on the extracted characteristic information, the disease grading information comprising grade information of a disease, a lesion type, a lesion location, and a number of lesions included by the disease; and constructing output information using the disease grading information;

wherein the operations further comprise establishing the disease grading model, and the establishing the disease grading model comprises:

extracting a reference lesion image from a reference lesion image set, extract a first reference lesion image from the reference lesion image, and obtain a lesion detection submodel by training using the first reference lesion image, the first reference lesion image comprising a first lesion image and location information corresponding to the first lesion image, the first lesion image comprising at least one of: a venous ring image, a vein beading image, or a neovascular image, wherein the lesion detection submodel is used for recognizing the first lesion image, and outputting the location information corresponding to the first lesion image;

extracting a second reference lesion image from the reference lesion image, and obtain a lesion segmentation submodel by training using the second reference lesion image, the second reference lesion image comprising a second lesion image and region information corresponding to the second lesion image, the second lesion image comprising at least one of: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image; and establishing a corresponding relationship respectively between the reference fundus image, the location information and the region information, and grading information of retinopathy, and between the reference fundus image, the location information and the region information, and grading information of macular edema, and obtain a disease grading submodel by training using the corresponding relationship, wherein the disease grading model is used for outputting the grading information of the retinopathy and/or the grading information of the macular edema based on the corresponding relationship.

8. The apparatus according to claim 7, wherein the introducing the fundus image into a pre-trained disease grading model to obtain disease grading information comprises:

extracting location information of a first lesion image from the fundus image, the first lesion image comprising at least one of: a venous ring image, a vein beading image, or a neovascular image;

extracting region information of a second lesion image from the fundus image, the second lesion image comprising at least one of: a cup optic disc image, a microangioma image, a haemorrhagic spot image, an exudative spot image, or a cotton-wool spot image; and determining the disease grading information of the fundus image, based on the location information and the region information.

9. The apparatus according to claim 8, wherein the determining the disease grading information of the fundus image, based on the location information and the region information, comprises:

performing data processing on a retinopathy image and a macular edema image in the fundus image to obtain initial grading information of retinopathy and initial grading information of macular edema; and establishing a matching relationship respectively between the initial grading information of the retinopathy and the location information and the region information, and between the initial grading information of the macular edema and the location information and the region information, and construct disease grading information of the retinopathy and disease grading information of the macular edema respectively using the matching relationship.

10. The apparatus according to claim 7, wherein the obtaining a lesion detection submodel by training using the first reference lesion image comprises:

extracting the first lesion image and the location information corresponding to the first lesion image from the first reference lesion image;

establishing a first corresponding relationship between the first lesion image and the location information; and obtaining the lesion detection submodel by training based on the first corresponding relationship using a machine learning method.

11. The apparatus according to claim 7, wherein the obtaining a lesion segmentation submodel by training using the second reference lesion image comprises:

extracting the second lesion image and the region information corresponding to the second lesion image from the second reference lesion image;

establishing a second corresponding relationship between the second lesion image and the region information; and obtaining the lesion segmentation submodel by training based on the second corresponding relationship using a machine learning method.

12. The apparatus according to claim 7, wherein the obtaining a disease grading submodel by training using the corresponding relationship comprises:

determining a lesion type using a regional relationship between the region information and the reference fundus image;

determining characteristic information corresponding to the lesion type using a location relationship, the characteristic information comprising at least one of: quantity, position, or area;

establishing a third corresponding relationship respectively between the lesion type and the characteristic information and the grading information of the retinopathy, and between the lesion type and the characteristic information and the grading information of the macular edema; and obtaining the disease grading submodel by training based on the third corresponding relationship using a machine learning method.

13. A non-transitory computer storage medium storing a computer program, the computer program when executed by one or more processors, causes the one or more processors to perform operations, the operations comprising:

acquiring a fundus image;

introducing the fundus image into a pre-trained disease grading model to obtain disease grading information, the disease grading model being used for extracting characteristic information from a lesion image contained in the fundus image, and generating the disease grading information based on the extracted characteristic information, the disease grading information comprising grade information of a disease, a lesion type, a lesion location, and a number of lesions included by the disease; and constructing output information using the disease grading information;

wherein the operations further comprise establishing the disease grading model, and the establishing the disease grading model comprises:

extracting a reference lesion image from a reference lesion image set, extract a first reference lesion image from the reference lesion image, and obtain a lesion detection submodel by training using the first reference lesion image, the first reference lesion image comprising a first lesion image and location information corresponding to the first lesion image, the first lesion image comprising at least one of: a venous ring image, a vein beading image, or a neovascular image, wherein the lesion detection submodel is used for recognizing the first lesion image, and outputting the location information corresponding to the first lesion image;

extracting a second reference lesion image from the reference lesion image, and obtain a lesion segmentation submodel by training using the second reference lesion image, the second reference lesion image comprising a second lesion image and region information corresponding to the second lesion image, the second lesion image comprising at least one of: a cup optic disc image, a microangioma image, a haemorrhagic spot image, an exudative spot image, or a cotton-wool spot image, wherein the lesion segmentation submodel is used for recognizing the second lesion image, and outputting the region information corresponding to the second lesion image; and establishing a corresponding relationship respectively between the reference fundus image, the location information and the region information, and grading information of retinopathy, and between the reference fundus image, the location information and the region information, and grading information of macular edema, and obtain a disease grading submodel by training using the corresponding relationship, wherein the disease grading model is used for outputting the grading information of the retinopathy and/or the grading information of the macular edema based on the corresponding relationship.

\* \* \* \* \*